United States Patent [19]

Clark, III

[11] Patent Number: 4,576,143

[45] Date of Patent: * Mar. 18, 1986

[54] METHOD OF IMMUNE MODIFICATION BY MEANS OF EXTRACORPOREAL IRRADIATION OF THE BLOOD

[76] Inventor: William T. Clark, III, No. 6 Davis Blvd., New Orleans, La. 70121

[ * ] Notice: The portion of the term of this patent subsequent to Mar. 30, 1999 has been disclaimed.

[21] Appl. No.: 658,436

[22] Filed: Oct. 5, 1984

[51] Int. Cl.⁴ .............................................. D61M 1/03
[52] U.S. Cl. ..................................... 128/1 R; 604/20
[58] Field of Search .................... 604/20, 21; 128/395, 128/1 R

[56] References Cited

U.S. PATENT DOCUMENTS

| 2,099,511 | 11/1937 | Caesar | 604/20 |
| 4,181,728 | 1/1980 | Swartz | 604/20 |
| 4,321,918 | 3/1982 | Clark, III | 604/20 |

FOREIGN PATENT DOCUMENTS 492770  3/1930  Fed. Rep. of Germany ...... 128/395

Primary Examiner—William E. Kamm
Attorney, Agent, or Firm—Littlepage & Webner

[57] ABSTRACT

In order to modify the immune system in humans having symptoms of a disorder of the immune system characterized by the presence of lymphocytes not apparently activated such lymphocytes are deactivated by a limited and closely controlled extracorporeal irradiation of an intensity and duration sufficient to cause the symptoms to disappear.

3 Claims, 9 Drawing Figures

METHOD OF IMMUNE MODIFICATION BY MEANS OF EXTRACORPOREAL IRRADIATION OF THE BLOOD

BACKGROUND AND OBJECTS OF THE INVENTION

In diseases which require immune management, the treating physician aims to replace specific undesirable immune responses with healthier, more beneficial immunity. Many illnesses are characterized by undesirable, overly active immune responses whereas other diseases are characterized by insufficiently effective immune activity.

Reference is made to U.S. Pat. No. 4,321,918, where it is shown that extracorporeal irradiation of the blood (ECIB) can be used to selectively suppress immunity to transplants while leaving the general immunity unimpaired. In that patent, a method of treatment was described in which the immune system of the body was taught by ECIB, selectively to disregard the "foreign body" aspect of the transplant which causes rejection symptoms and consequent failure of the transplant to occur, without affecting the general immunity of the body which is available to fight other disease.

It is an object of this invention to provide a method of immune modification in human patients by means of extracorporeal irradiation of blood.

It is a further object of this invention to provide a method of treatment for auto-immune diseases and for diseases characterized by immune insufficiency.

DESCRIPTION OF THE INVENTION

It has now been found by subsequent research that extracorporeal irradiation of the blood which produces a selective suppression of immunity may be used successfully to treat auto-immune diseases. Furthermore, if extracorporeal irradiation of the blood is continued past the point of lymphocyte suppression then the general immunity increases, while the specific, undesired immunity remains decreased. This rise in general immunity may be used to treat disease characterized by insufficient immunity, such as malignant neoplastic disease.

In these diseases treated by use of the method of this invention, none of the cells are from sources which are foreign to the patient's body, such as are present in transplant patients. In transplant patients the human body, which normally has immune defenses to foreign cells, must have the immunity suppressed by methods such as that of U.S. Pat. No. 4,321,918 or by drug therapy or other means. In the diseases of the immune system to which this invention is directed, there are no cells present from sources outside the body. Non-limiting examples of auto-immune diseases are lupus erythematosus, multiple sclerosis, scleroderma, etc. Immune insufficiency diseases include those which produce malignant neoplasms such as cancerous tumors or leukemia.

In auto-immune disease, activated lymphocytes are directed against the host. In cancer and other immune insufficiency diseases the activated lymphocytes are inadequately directed against the disease. According to this invention, immune modification is effected, the immune memory no longer produces the same undesirable lymphocytes, and a different lymphocyte population emerges, shown by removal of the disease symptoms. In auto-immune disease the disease condition recedes and in malignant neoplastic disease the host controls the neoplasm causing a cessation of cell proliferation.

The procedure for extracorporeal irradiation of the blood is simple and painless to the patient, and is described with reference to the drawings.

Figure 1:
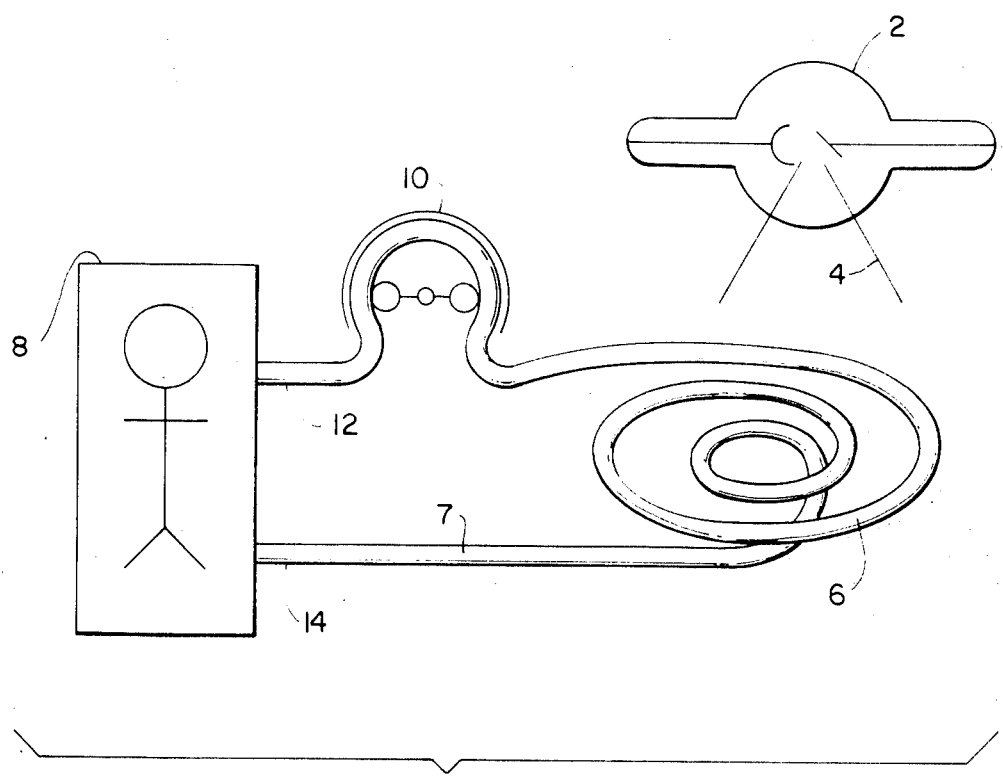
FIG. 1 is a diagram of the apparatus.
Figure 2:
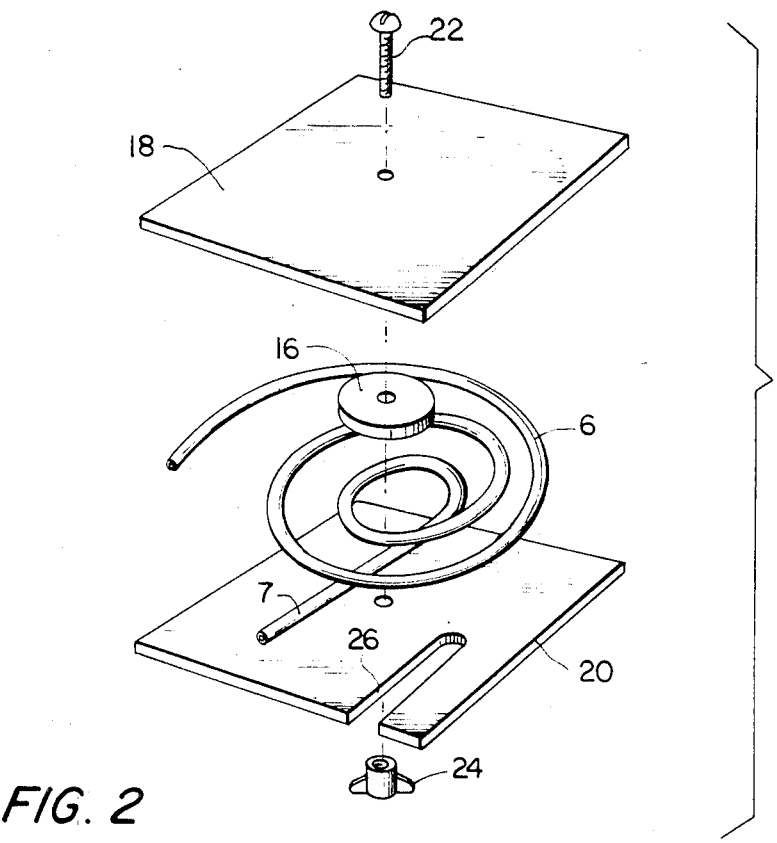
FIG. 2 is an exploded view of the spiral tubing disc and mounting.
Figure 3:
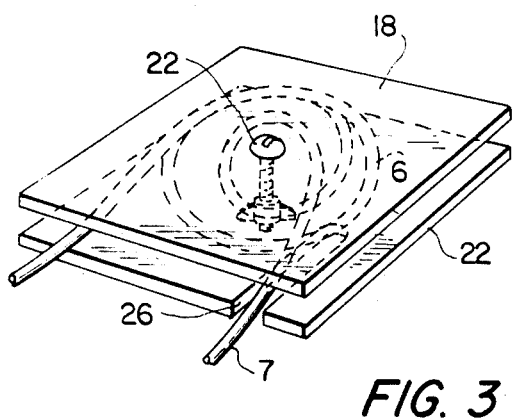
FIG. 3 is a perspective view of the mounted spiral tubing disc.

The apparatus used, and shown in FIGS. 1–3 is the same as that disclosed in my previous patent, U.S. Pat. No. 4,321,918. Referring to the drawings, FIG. 1 illustrates a source of x-rays 2 emitting a beam 4 which impinges upon the spiral disc 6 of tubing 7. The patient 8 is cannulated so that a blood pump 10 can pump from an artery or other appropriate vessel 12 through the spiral disc 6 and back to the patient's vein 14.

Referring to FIG. 2, the tubing 7 of spiral disc 6 is wound onto a bobbin 16 between two low-density plastic plates (polycarbonate, for example) 18 and 20 which keep the tubing flat and thereby keep the field substantially uniform. A screw 22 and a wing nut 24 keep the assembly together; a relief slot 26 for the tubing end allows the disc to remain flat. The spiral disc assembly may slide into a drawer in a shielded box beneath the source of radiation. The spiral may be wound in multiple layers in order to increase the radiation dose permitting a faster flow rate. The apparatus is shown assembled at FIG. 3.

The tubing used for extracorporeal irradiation is primed with normal saline and heparin before connection to the patient. The patient is then systemically heparinized and connected to the tubing via conventional cannulation with arteriovenous shunt or fistula.

The tubing 7 used for the extracorporeal irradiation link is any tubing suitable for an extra corporeal blood circuit and capable of allowing the passage of x-rays. For example, sterilized polyvinyl chloride tubing is suitable.

The radiation dose received by the blood as it passes through the radiation field is the transit dose. The total dose per treatment is the transit dose multiplied by the number of times the blood passes through the radiation field each treatment. The general treatment regimen is to irradiate the blood daily while passing it through an extracorporeal irradiation link for approximately one hour. For example, if the transit dose used is 31.1R, a total dose per daily treatment of 31.1R to 62.2R may be provided in an approximately one hour treatment, by irradiating the blood in one to two transits through the extracorporeal irradiation link. Higher or lower doses may be used according to the responsiveness of the patient. The radiation dose is critical as it must be enough to suppress the activated lymphocytes without killing them while allowing a different population of lymphocytes to emerge.

Used according to the subject process, extracorporeal irradiation of the blood has no harmful side effects to the patient's body since the dosage is very low and the irradiation takes place outside the body. The patient's blood may even be irradiated continuously so long as the total dose resulting from the blood transits does not exceed that necessary to suppress the undesired lymphocytes without killing them, while allowing the desirable lymphocyte cell population to emerge.

The following case study examples demonstrate the immune modification of the invention, evidenced by lymphocyte stimulation studies, shown graphically in FIGS. 4-9. All the patients showed a rise in immunity. The treatment is discontinued when the desired immune status is achieved, as determined by immune studies and by the relief of symptoms.

The patient statistics are summarized in Table 1.

TABLE 1

| PATIENT | SEX | AGE | DIAGNOSIS | NUMBER OF SERIES OF TREATMENTS | TOTAL NUMBER OF DAILY TREATMENTS | DAILY DOSE | IMMUNE MODIFICATION? |
|---------|-----|-----|-----------|-------------------------------|----------------------------------|------------|----------------------|
| AP | F | 48 | Neoplastic | 3 | 19 | 62.2 R | YES |
| MM | F | 65 | Neoplastic Auto-immune | 1 | 14 | 38.9 R | YES |
| RT | M | 49 | Auto-Immune | 3 | 40 | 62.2 R | YES |
| CA | M | 65 | Neoplastic | 1 | 7 | 38.9 R | YES |
| EB | M | 72 | Neoplastic | 1 | 12 | 46.6 R | YES |
| NH | M | 66 | Neoplastic | 1 | 9 | 38.9 R | YES |

The six case histories presented below illustrate each of the three situations where immune modification is required and desired, i.e., an increase in general immunity such as is required in treatment of immune insufficiency disease; an increase in general immunity and a decrease in specific immunity, for example, in malignant neoplastic disease combined with auto-immune disease; and where only decrease in specific immunity is needed, as in auto-immune disease.

EXAMPLE 1

Patient AP: Malignant neoplasm.

Female, age 48, with a diagnosis of disseminated, inoperable, terminal cancer of the colon.

The patient was presented to extracorporeal irradiation as a last resort, since other therapy was to no avail. Upon presentation, the patient was unable to stand upright without extreme uncontrollable pain. She was unable to eat, in great emotional trauma, and heavily medicated with narcotic pain killers which did not adequately control the pain.

Extracorporeal irradiation of the blood was conducted daily with a transit dose of 31.1R for a period of approximately one hour, resulting in a total daily dose of 62.2R. The initial series was for nine treatments followed by two series of five treatments each, at approximately one month intervals.

Figure 4:
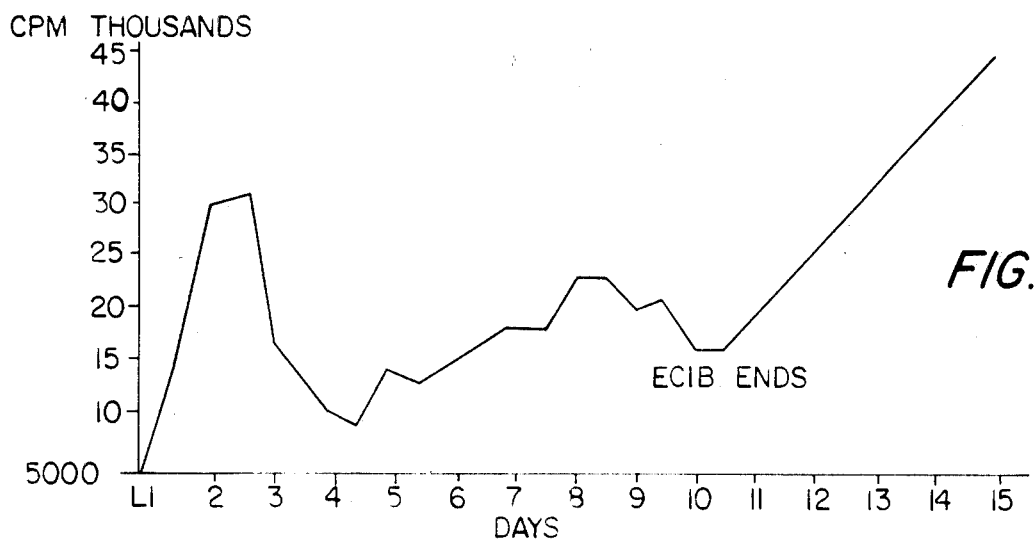
FIGS. 4–9 show graphically the results of lymphocyte stimulation studies in Patient Examples 1–6.

The patient responded quickly with a lessening of pain and a return of appetite and feeling of well-being. Subsequent to the first series, she was discharged from the hospital without pain and was withdrawn from pain medication. She was able to reenter the life of the community of which she was a resident. She was able to drive an automobile and returned for her subsequent series of treatments as an outpatient. Thermographic analysis documented greatly decreased inflammation of the bowel during the course of ECIB therapy. Her lymphocyte stimulation studies are illustrated in FIG. 4, and demonstrate immune modification. The patient subsequently died of complications resulting from previously incurred surgically-produced adhesions, and autopsy confirmed that the previously massive tumor had shrunk from its former size and condition and was comprised largely of dying and necrotic tissue.

EXAMPLE 2

Patient MM: Malignant neoplasm and auto-immune disease.

Female, age 65, with a diagnosis of terminal disseminated cancer and systemic lupus erythematosus characterized by a profound thrombocytopenia and a resumed lupus nephritis. She exhibited diffuse erythematous patches.

The patient was presented to extracorporeal irradiation as a last resort, since other therapy had not been successful. The patient was moderately hypervolemic; pre-treatment platelet levels were so low as to require transfusion. She was agitated with pain controlled by medication. Platelet destruction was continuing until ECIB treatment commenced.

Extracorporeal irradiation of the blood was conducted daily with a transit dose of 31.1R for approximately one hour per day resulting in a daily dose of 38.9R. The patient was treated 14 times.

Figure 5:
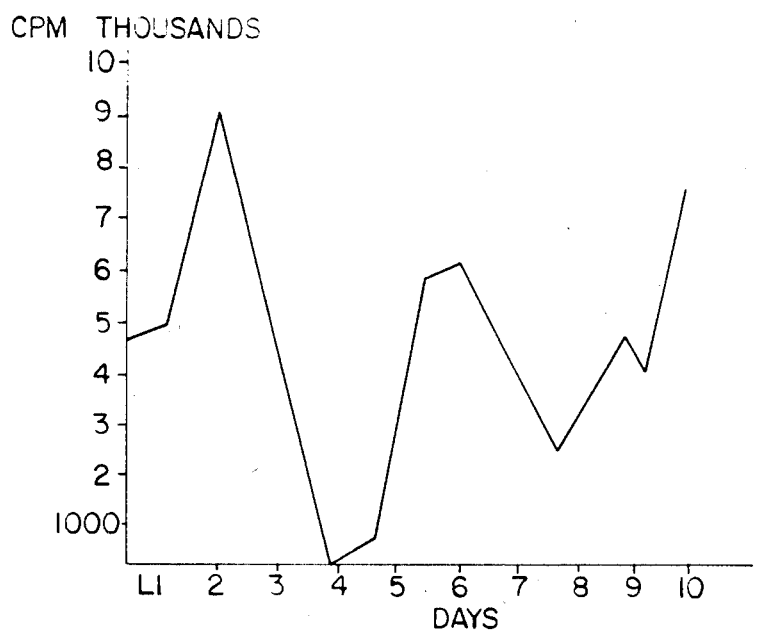

The patient responded quickly with a lessening of pain and a loss of excess fluid. The erythematous discolored patches decreased or disappeared altogether. Platelet levels stabilized during treatment, and then platelet levels rose quickly, and at the end of the series the platelet count was approximately 3 times pre-treatment level. Her lymphocyte stimulation studies are illustrated in FIG. 5 and demonstrate modification of immunity.

EXAMPLE 3

Patient RT: Auto-immune disease.

Male, age 49, with a diagnosis of multiple sclerosis.

The patient was presented to extracorporeal irradiation because other therapy had been to no avail in spite of progressive disease of some ten years duration, characterized by increasing loss of bowel and bladder control and increasing motor difficulties such as inability to walk unassisted or climb short steps.

Prior to receiving extracorporeal irradiation, and on one occasion simultaneously, the patient was treated with biocompatible hemoperfusion (as described in U.S. Pat. No. 4,048,064) in order to plasmapherese humoral immune components and thereby accelerate control of cellular immunity.

Figure 6:
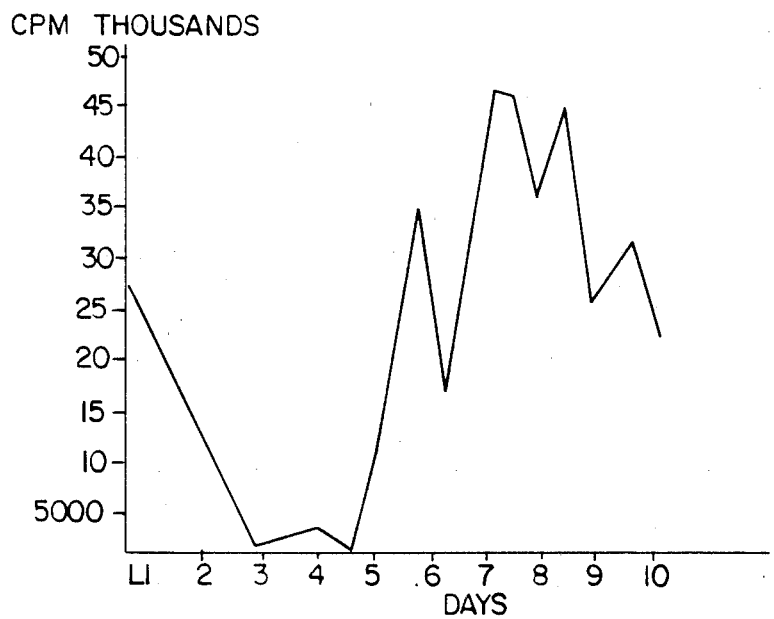

The patient responded very quickly to extracorporeal irradiation which was at first manifest by an improved sense of confidence and well-being. As the treatments progressed, bowel and bladder control returned, and the patient was able to climb stairs and walk with far greater ease. The patient was treated daily in three series of treatments. The first series was 7 treatments, the second was 10 treatments, and the third was 23 treatments. Treatment was one hour daily at a transit dose of 31.1R for a total daily dose of approximately 62.2R. The patient's lymphocyte stimulation studies are illustrated at FIG. 6. The patient's condition has stabilized in the improved condition.

EXAMPLE 4

Patient CA: Malignant neoplasm.

Male, age 65, with a diagnosis of terminal leukemia.

The patient was introduced to ECIB when all other therapy had been to no avail. Upon presentation, the patient exhibited acute distress, agitation, difficulty breathing, edema, rapidly rising white cell count, very extremely elevated uric acid, rapidly advancing kidney failure, and pain controlled by medication.

Because the patient had great difficulty breathing and remaining sedentary, treatment was necessarily shortened. ECIB was begun when the patient was near death. The patient was treated 30 min. to 1 hr. for 6 days at 31.1 to 46.6R. At the end of his sixth treatment, his white count had stabilized, and his uric acid had completely returned to normal indicating that cell destruction characteristic of the disease was ceasing. Thermographic analysis documented much decreased inflammation of the lymphatic system.

Figure 7:
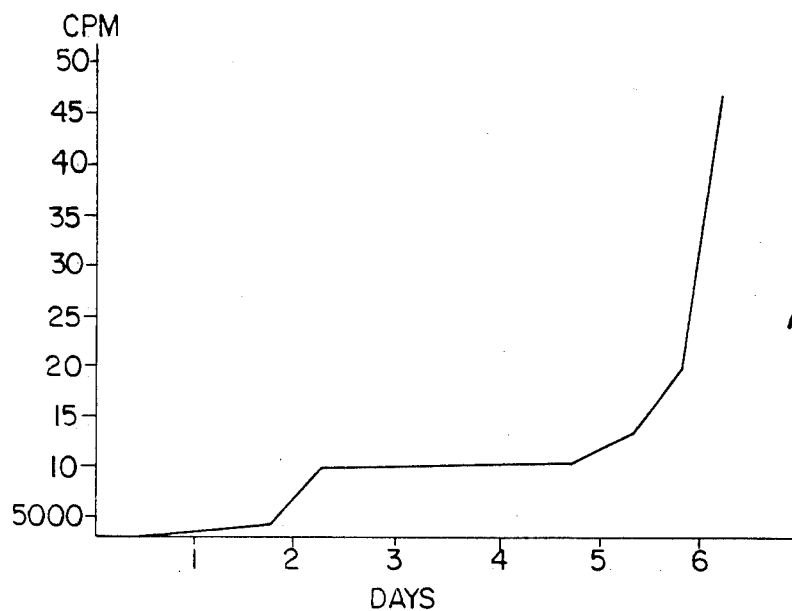

The curve of FIG. 7 graphically illustrates a case wherein the inappropriateness of the activation of the patient's lymphocytes was that it was a zero activation, this being a characteristic of malignant neoplasm. After commencing the treatment the count per minute of lymphocyte stimulation rose slightly, but the patient's symptoms were such that the inappropriateness of activation persisted. After the commencement of the second day of treatment, the count per minute rose to slightly more than 10,000 counts per minute, but the persistence of the symptoms lasted until near the commencement of the fifth day, whereupon the counts per minute commenced to rise and during about the middle of the fifth day the counts per minute rose greatly and soon thereafter rose abruptly to near 50,000 counts per minute and the symptoms of the disorder subsided.

The patient's immune studies shown in FIG. 7 demonstrate that immune modification had taken place.

EXAMPLE 5

Patient EB: Malignant neoplasm.

Male, age 72, with a diagnosis of terminal cancer of the bone.

The patient was introduced to ECIB when all other therapy had been to no avail. Upon presentation, the patient suffered painful walking and hip movement. Uric acid was moderately elevated, and his white count was very low.

The patient was given 12 daily 1 hr. treatments at a dose rate of 46.6R.

At termination of treatment, the patient could walk and turn with greater ease, pain was decreased, uric acid was reduced, and his white count had increased to normal.

Figure 8:
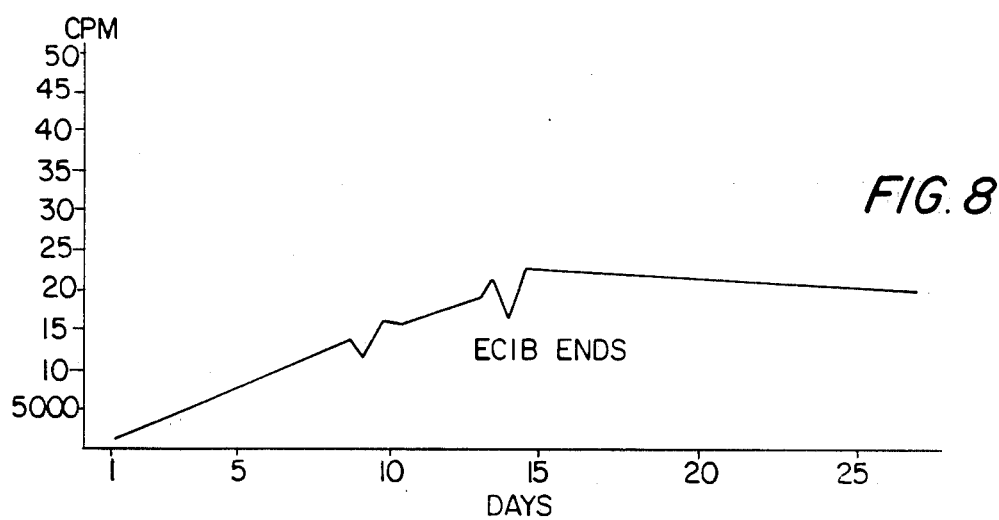

The patient's lymphocyte stimulation studies demonstrating immune modification are shown in FIG. 8.

EXAMPLE 6

Patient NH: Malignant neoplasm.

Male, age 66, diagnosed as having terminal cancer of the prostate.

The patient was presented to ECIB when all other therapy had been to no avail. The patient was mentally disoriented with complaints of discomfort, agitation, and pain which was controlled by medication. His white cell count was very low, and his urine output was inadequate.

The patient was treated 1 hr. per day for 9 days with a daily dose of 41.4R to 46.6R. At termination of treatment, his white count had doubled to become normal, urine output had increased 600% to become normal, and pain and discomfort decreased.

Figure 9:
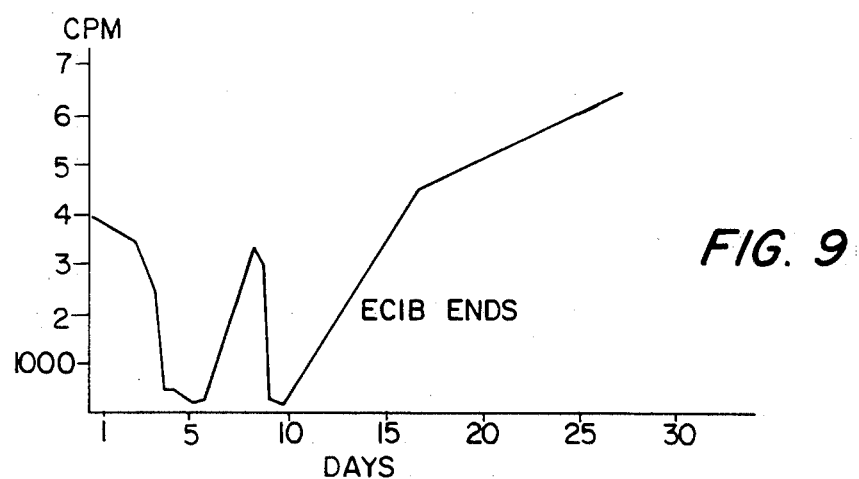

The patient's lymphocyte stimulation studies showing immune modification are shown in FIG. 9.

The curves in FIG. 9 graphically describe the change in the lymphocyte activation where repetitive doses were required to affect the desired change. The lymphocyte activation of a patient having symptoms of immune disorder was measured at the start, exhibiting a count of 4,000 per minute. At the end of four days, the count had dropped to about 500 counts per minute, denoting deactivation of the inappropriately activated lymphocytes, and on the fifth day the count had dropped to less than 500 counts per minute. During the sixth day, the counts per minute rose to about 3,500 per minute, denoting the emergence of a new lymphocyte population, but since the symptoms of disorder persisted the emerged lymphocyte population also was not appropriately activated. The doses were continued and by the tenth day the count per minute had dropped to a count of 100 or 200 a minute, and after the tenth day the counts per minute rose concurrently with an abatement of the symptoms of immune disorder and the curve continued to rise until on about the 27th day, the counts per minute had risen to about 6,750 per minute, the absence of recurrence of the symptoms of disorder proving that the lymphocytes in the population of the patient's blood were not inappropriately activated.

Each of the patients here summarized unexpectedly greatly benefited in their physical well-being from treamtment by extracorporeal irradiation of the blood. The lymphocyte stimulation studies for each patient clearly demonstrate immune modification with this technique, and none of the patients suffered any undesirable side effects, even though before treatment conventional therapeutic possibilities had been exhausted. Using such a low suppressive dose of radiation to the blood does not cause cell death and apparently causes lymphocyte cell population shifts, because the activated lymphocytes are more radiosensitive than unactivated lymphocytes. For this reason, extracorporeal irradiation of the blood is preferably initiated when the offending lymphocyte population is active and the diseases exacerbate. Where it is desired to increase general immunity, extracorporeal irradiation is continued until sufficient immune virulence is achieved as successive lymphocyte populations emerge. Where it is desirable to selectively decrease specific immunity, extracorporeal irradiation is continued until that specific immunity is decreased followed by an increase in the general immunity. Using the technique described, blood cell counts will not decrease, massive cell death will not occur, and the immune status of the patient will be desirably modified, leading to improved health and well-being.

For each of these six patients, x-ray irradiation was used, though other types of radiation, for example, ultraviolet or other type of ionizing actinic radiation may be used. The x-ray machine used was a G.E. Maxima R with a ½ mm. Al. filter, operated at 100 kv with a 7ma. current delivering a dose rate of 155.5R/min. to the tubing spiral disposed at 15 cm from the target electrode. The resultant transit doses were 31.1R per minute. In each instance, the irradiation was considered to be adequate when modification of the immune system was shown by a standard Lymphocyte Stimulation Test, with no cell death and blood cell counts unimpaired. If the activated lymphocytes were to be killed, the patient's system would tend to be triggered into creating a replacement population of identical undesirable lymphocytes. The treatments of a patient are continued from day-to-day until the symptoms of the disease subside.

Because of the relatively short life span of the blood of a human being, the cumulative effects of the extracorporeal irradiation are not a factor, as are the cumulative effects when body tissues are irradiated. The blood which has been irradiated during one series of daily treatments will not likely be present during a subsequent series of treatments.

Total doses per treatment ranging from 24.4R to 93.3R have been sufficient to suppress the activated lymphocytes and the immune memory and to allow a different lymphocyte population to emerge. Immune modification is demonstrated by the fact that the different lymphocyte population which emerges does not cause the disease symptoms. The patient's disease symptoms subside when the cell population shifts. By treatment with this invention, the immune system is deactivated until another cell population emerges in which the new activated lymphocytes correct the error of the body's immune system, causing the disease symptoms to recede. The reproduction of the cells has been affected.

Variations and modifications of this invention can be effected within the spirit and scope of the invention as described above and as defined in the appended claims.

I claim:

1. A method for immune modification in a human patient having symptoms of a disorder of the immune system characterized by the presence of lymphocytes which are not appropriately activated which comprises:
deactivating those lymphocytes which are not appropriately activated by passing the patient's blood through an extracoporeal link, and irradiating it while in transit through the link with a transit dose to render the not appropriately activated lymphocytes inactive but less than that required to significantly diminish the patient's lymphocyte count, and continuing such irradiation until a different lymphocyte population emerges, which different lymphocyte population is characterized by lymphocytes which have not been inappropriately activated, said irradiation continuing until the symptoms of the disorder have subsided, and further continuing the aforesaid irradiation of the patient's blood if the symptoms of disorder reappear.

2. A method of claim 1 wherein the total dose per treatment is between about 24.4R and about 93.3R.

3. A method of claim 1 wherein the general immunity of the patient is increased.

* * * * *